(12) United States Patent
Lowndes et al.

(10) Patent No.: US 6,201,012 B1
(45) Date of Patent: *Mar. 13, 2001

(54) COMPOSITION FOR CONTROLLING PARASITES

(75) Inventors: Philip Anthony Lowndes, Cambridge (GB); Stefan Kemmethmüller, Freiburg (DE); Steven Craig Parks, Greensboro; Douglas Irvin Hepler, High Point, both of NC (US)

(73) Assignee: Novartis Animal Health US, Inc., Greensboro, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/399,503

(22) Filed: Sep. 20, 1999

Related U.S. Application Data

(62) Division of application No. 08/894,579, filed on Jan. 23, 1998, now Pat. No. 5,994,395.

(30) Foreign Application Priority Data

Feb. 24, 1995 (CH) .................................... 541/95
Feb. 15, 1996 (WO) ................... PCT/EP96/00658

(51) Int. Cl.$^7$ .................................... A01N 43/16
(52) U.S. Cl. ......................... 514/460; 514/819
(58) Field of Search ..................... 514/460, 819

(56) References Cited

U.S. PATENT DOCUMENTS

| | | | |
|---|---|---|---|
| 3,950,360 | 4/1976 | Aoki et al. | 260/343.2 R |
| 4,199,569 | 4/1980 | Chabala et al. | 424/180 |
| 4,310,519 | 1/1982 | Albers-Schonberg et al. | 424/181 |
| 4,346,171 | 8/1982 | Takiguchi et al. | 435/119 |
| 4,547,520 | 10/1985 | Ide et al. | 514/450 |
| 4,677,127 | 6/1987 | Böger | 514/346 |
| 4,696,945 | 9/1987 | Frei et al. | 514/450 |
| 4,959,386 | 9/1990 | Frei et al. | 514/450 |
| 4,988,824 | 1/1991 | Maulding et al. | 549/264 |
| 5,994,395 | * 11/1999 | Lowndes et al. | 514/460 |

FOREIGN PATENT DOCUMENTS

| | | |
|---|---|---|
| 0 242 502 | 10/1997 | (EP) . |
| 2 220 856 | 1/1990 | (GB) . |
| 86/03941 | 7/1986 | (WO) . |
| 95/33380 | 12/1995 | (WO) . |

OTHER PUBLICATIONS

Bull. Soc. France Parasit, 8, 1990.
Interceptor, Flavor Tabs, Aug. 1994.
Lowndes, Program Product Profile, Feb. 4, 1992.
Merck Index, p. 128, 753, 887.

* cited by examiner

*Primary Examiner*—Jose'G. Dees
*Assistant Examiner*—Alton Pryor
(74) *Attorney, Agent, or Firm*—Michael P. Morris; William A. Teoli

(57) ABSTRACT

The present invention relates to a composition for controlling parasites, in and on animals, which comprises, as active ingredient, a combination, in variable proportions, of at least one parasiticidally active compound, in free form or in salt form, selected from the N-phenyl-N'-benzoyl-urea class of substances, and at least one parasiticidally active compound, in free form or in salt form, selected from the milbemycin, avermectin, milbemycin oxime, moxidectin, ivermectin, abamectin and doramectin classes of substances and the derivatives thereof; to a method of controlling these pests; to a process for the preparation of this composition; and to the use of this composition.

11 Claims, No Drawings

COMPOSITION FOR CONTROLLING PARASITES

This application is a Division of application Ser. No. 08/894,579 filed Jan. 23, 1998 now U.S. Pat. No. 5,994,395.

The present invention relates to a composition that comprises a combination of at least two parasiticidally active substances and that is suitable for controlling pests in and on animals, to a method of controlling these pests, to a process for the preparation of this composition, and to the use of this composition.

Certain compositions for controlling pests in and on animals are proposed in the literature. The properties of these known compositions are not always, however, entirely satisfactory, and, therefore, there is a need to make available further parasiticidally active compositions, especially for the control of insects, representatives of the order Acarina or parasitic worms, for example helminths. This problem is solved according to the invention by the provision of the instant composition.

The present invention accordingly relates to a composition for controlling parasites, in and on animals, which comprises, as active ingredient, a combination, in variable proportions, of at least one parasiticidally active compound, in free form or in salt form, selected from the N-phenyl-N'-benzoyl-urea class of substances, and at least one parasiticidally active compound, in free form or in salt form, selected from the milbemycin, avermectin, milbemycin oxime, moxidectin, ivermectin, abamectin and doramectin classes of substances and the derivatives thereof.

The invention relates preferably to a composition which comprises, as active ingredient, at least one compound of formula

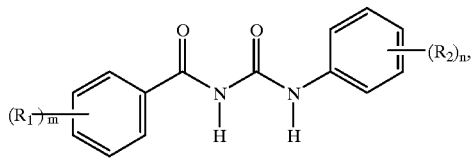

(I)

wherein $R_1$ is halogen, $C_1$–$C_8$alkyl, $C_3$–$C_8$cycloalkyl, halo-$C_3$–$C_8$cycloalkyl, halo-$C_1$–$C_8$alkyl, $C_1$–$C_8$alkoxy, $C_1$–$C_4$alkoxy-$C_1$–$C_4$alkyl or halo-$C_1$–$C_8$alkoxy;

$R_2$ is halogen, $C_1$–$C_8$alkyl, $C_3$–$C_8$cycloalkyl, halo-$C_1$–$C_8$alkyl, $C_1$–$C_8$alkoxy, $C_3$–$C_8$cycloalkoxy, halo-$C_1$–$C_8$alkoxy, aryloxy or heteroaryloxy, substituted aryloxy or heteroaryloxy or a group —$CH_2$—O—N=$C(R_3)R_4$;

$R_3$ and $R_4$ are each independently of the other $C_1$–$C_4$alkyl, $C_3$–$C_8$cycloalkyl or aryl, each of which is unsubstituted or substituted;

m is 0 to 5, where, when m is greater than 1, the radicals $R_1$ are independent of one another; and n is 0 to 5, where, when n is greater than 1, the radicals $R_2$ are independent of one another;

in free form or in salt form;
and at least one compound of formula

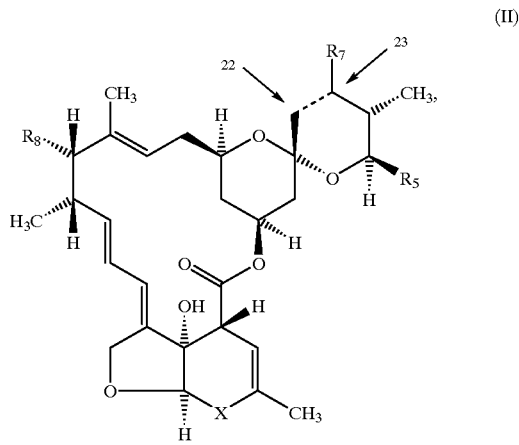

(II)

wherein $R_5$ is $C_1$–$C_4$alkyl or $C_2$–$C_4$alkenyl;

the bond between the atoms 22 and 23 is a single bond or a double bond;

—X— is a group

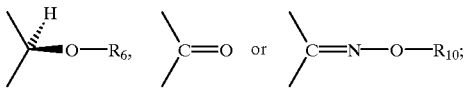

$R_6$ is hydrogen, unsubstituted or substituted $C_1$–$C_8$alkyl, unsubstituted or substituted aryl, —C(=O)$R_{17}$ or —Si$(R_{18})(R_{19})(R_{20})$;

$R_7$ is hydrogen or hydroxy, $R_7$ being hydrogen when the bond between the atoms 22 and 23 is a double bond;

$R_8$ is hydrogen, $C_1$–$C_8$alkyl, $C_2$–$C_8$alkenyl, aryl or a group —$OR_9$ or —$SR_9$;

$R_9$ is $C_1$–$C_8$alkyl, $C_2$–$C_8$alkenyl, $C_2$–$C_8$alkynyl, aryl, C(=O)$R_{16}$, substituted $C_1$–$C_8$alkyl, $C_2$–$C_8$alkenyl, $C_2$–$C_8$alkynyl or aryl, or an unsubstituted or substituted heterocyclic radical;

$R_{10}$ is hydrogen, unsubstituted or substituted $C_1$–$C_8$alkyl, aryl-$C_1$–$C_4$alkyl, —$(CH_2)_oCOR_{11}$ or —$SO_2$—$R_{15}$;

$R_{11}$ is hydrogen, $C_1$–$C_8$alkyl, aryl-$C_1$–$C_8$alkyl, $C_2$–$C_8$alkenyl, $C_2$–$C_8$alkynyl, $C_1$–$C_8$alkoxy, $C_2$–$C_8$alkenyloxy, $C_2$–$C_8$alkynyloxy, aryl, aryloxy, —$N(R_{12})R_{13}$, —$(CH_2)_pCOOR_{14}$, or $C_1$–$C_8$alkyl or $C_1$–$C_8$alkoxy substituted by $C_1$–$C_4$alkoxy, halogen or by nitro, or aryl, aryloxy or aryl-$C_1$–$C_8$alkyl substituted by $C_1$–$C_4$alkyl, halo-$C_1$–$C_4$alkyl, $C_1$–$C_4$alkoxy, halo-$C_1$–$C_4$alkoxy, halogen or by nitro;

$R_{12}$ and $R_{13}$ are each independently of the other hydrogen, $C_1$–$C_8$alkyl, phenyl, or $C_1$–$C_8$alkyl or phenyl substituted by $C_1$–$C_4$alkoxy, halogen or by nitro;

$R_{14}$ is hydrogen or unsubstituted or substituted $C_1$–$C_8$alkyl;

$R_{15}$ is $C_1$–$C_8$alkyl or aryl, each of which is unsubstituted or substituted;

$R_{16}$ is hydrogen, $C_1$–$C_8$alkyl, $C_1$–$C_8$alkoxy or aryl, each of which is unsubstituted or substituted;

$R_{17}$ is hydrogen, $C_1$–$C_8$alkyl, $C_1$–$C_8$alkoxy or aryl, each of which is unsubstituted or substituted;

$R_{18}$, $R_{19}$ and $R_{20}$ are each independently of the others $C_1$–$C_8$alkyl, $C_1$–$C_8$alkoxy or aryl, each of which is unsubstituted or substituted;

o is 0, 1, 2, 3 or 4; and p is 0, 1, 2, 3 or 4;

in free form or in salt form.

A compound I or II, which has at least one basic centre, can form, for example, acid addition salts. These acid addition salts are formed, for example, with strong inorganic acids, such as mineral acids, for example perchloric acid, sulfuric acid, nitric acid, nitrous acid, a phosphoric acid or a hydrohalic acid, with strong organic carboxylic acids, such as unsubstituted or substituted, for example halogen-substitutled, $C_1$–$C_4$alkanecarboxylic acids, for example acetic acid, or unsaturated or saturated dicarboxylic acids, for example oxalic acid, malonic acid, succinic acid, maleic acid, fumaric acid or phthalic acid, or hydroxycarboxylic acids, for example ascorbic acid, lactic acid, malic acid, tartaric acid or citric acid, or benzoic acid, or with organic sulfonic acids, such as unsubstituted or substituted, for example halogen-substituted, $C_1$–$C_4$alkane- or arylsulfonic acids, for example methane- or p-toluenesulfonic acid. A compound I or II, which has at least one acidic group, can form salts with bases. Suitable salts with bases are, for example, metal salts such as alkali metal salts or alkaline earth metal salts, for example sodium salts, potassium salts or magnesium salts, or salts with ammonia or with an organic amine, such as morpholine, piperidine, pyrrolidine, a mono-, di- or tri-lower-alkylamine, for example ethyl-, diethyl-, triethyl- or dimethylpropylamine, or a mono-, di- or trihydroxy-lower-alkylamine, for example mono-, di- or triethanolamine. Moreover, corresponding internal salts may also be formed, where possible. Preferred salts within the scope of the invention are veterinarily advantageous salts. Due to the close relationship between a compound I or II in free form and in the form of the salts thereof, a free compound I or II, or the salts thereof, respectively, are to be understood analogously hereinabove and hereinafter as meaning, if appropriate, also the corresponding salts and the free compounds I or II, respectively. Generally preferred is, in each case, the free form.

The compounds of formula II wherein X is

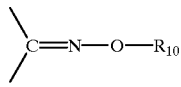

may occur as syn-isomers or anti-isomers in respect of the double bond. According to the invention, both forms are included, both the pure isomers and mixtures of isomers being meant.

Unless defined otherwise, the general terms used hereinbefore and hereinafter have the meanings given below.

Halogen—as a group per se and as a structural unit of other groups and compounds, such as of haloalkyl and haloalkoxy, —is fluorine, chlorine, bromine or iodine, especially fluorine, chlorine or bromine, more especially fluorine or chlorine.

Unless defined otherwise, groups and compounds containing carbon each preferably contain from 1 up to and including 20, preferably from 1 up to and including 18, most preferably from 1 up to and including 10, especially from 1 up to and including 6, most especially from 1 up to and including 4, especially from 1 up to and including 3, carbon atoms.

Alkyl—as a group per se and as a structural unit of other groups and compounds, such as of haloalkyl, alkoxy and haloalkoxy, —is either straight-chained, e.g. methyl, ethyl, n-propyl, n-butyl, n-hexyl, n-octyl, n-decyl, n-dodecyl, n-hexadecyl or n-octadecyl, or branched, e.g. isopropyl, isobutyl, sec-butyl, tert-butyl, isopentyl, neopentyl or isohexyl.

Alkenyl—as a group per se and as a structural unit of other groups, such as of alkenyloxy, —is straight-chained or branched alkenyl, e.g. vinyl, 1-methylvinyl, allyl, but-1-enyl or isopropenyl, especially allyl.

Alkynyl—as a group per se and as a structural unit of other groups and compounds, such as of alkynyloxy, —is e.g. ethynyl, prop-1-ynyl or but-1-ynyl, especially propargyl.

Halo-substituted carbon-containing groups and compounds, such as haloalkyl, halocycloalkyl and haloalkoxy, may be partially halogenated or perhalogenated, and, in the case of multiple halogenation, the halogen substituents may be identical or different. Examples of haloalkyl—as a group per se and as a structural unit of other groups and compounds, such as of haloalkoxy, —are methyl substituted by from one to three fluorine, chlorine and/or bromine atoms, such as $CHF_2$, $CF_3$ or $CH_2Cl$; ethyl substituted by from one to five fluorine, chlorine and/or bromine atoms, such as $CH_2CF_3$, $CF_2CF_3$, $CF_2CCl_3$, $CF_2CHCl_2$, $CF_2CHF_2$, $CF_2CFCl_2$, $CH_2CH_2Cl$, $CF_2$ $CHBr2$, $CF_2CHClF$, $CF_2CHBrF$ or $CClFCHClF$; propyl or isopropyl substituted by from one to seven fluorine, chlorine and/or bromine atoms, such as $CH_2CHBrCH_2$ $Br$, $CF_2CHFCF_3$, $CH_2CF_2CF_3$, $CF_2CF_2CF_3$, $CH(CF_3)_2$ or $CH_2CH_2CH_2Cl$; and butyl or one of its isomer substituted by from one to nine fluorine, chlorine and/or bromine atoms, such as $CF(CF_3)CHFCF_3$, $CF_2(CF_2)_2CF_3$ or $CH_2(CF_2)_2CF_3$.

Cycloalkyl—as a group per se and as a structural unit of other groups and compounds, such as of cycloalkoxy, —is cyclopropyl, cyclobutyl, cyclopentyl, cyclohexyl, cycloheptyl or cyclooctyl. Cyclopropyl is preferred.

Aryl is preferably phenyl or naphthyl, especially phenyl.

Heteroaryl is preferably an aromatic, monocyclic or bicyclic, ring system, which comprises one or two rings, selected from the group consisting of 5- and 6-membered rings, which is unsubstituted or substituted by one or two substituents, selected from the group consisting of chlorine, nitro, methyl and trifluoromethyl, and which contains 1 or 2 hetero atoms, selected from the group consisting of nitrogen, oxygen and sulfur atoms. Preferred are rings having one or two nitrogen hetero atoms, especially pyridyl, pyrimidyl and quinolyl, most especially unsubstituted pyridyl or pyrimidyl, chloro-pyridyl, trifluoromethyl-pyridyl, nitro-pyridyl, chloro-trifluoromethyl-pyridyl and chloroquinolyl.

Especially preferred within the scope of the present invention is a composition, that comprises, as active ingredient, on the one hand at least one compound, selected from any one of the following groups (1) to (11):

(1) a compound of formula I, wherein $R_1$ is halogen, especially fluorine, most especially wherein $(R_1)_m$ is 2,6-difluorine;

(2) a compound of formula I, wherein $R_2$ is halogen, halo-$C_1$–$C_4$alkyl, halo-$C_1$–$C_4$alkoxy or substituted pyridyloxy, and n is 1, 2, 3 or 4, especially wherein $R_2$ is fluorine, chlorine, halo-$C_1$–$C_3$alkoxy or chlorofluoromethyl-pyridyloxy;

(3) the compound 1-[2,5-dichloro-4-(1,1,2,3,3,3-hexafluoroprop-1-oxy)phenyl]-3-(2,6-difluorobenzoyl)-urea (Lufenuron);

(4) the compound 1-(3-(3-chloro-5-trifluoromethyl-2-pyridyloxy)-4-chloro-phenyl)-3-(2,6-difluorobenzoyl)-urea (Fluazuron);

(5) the compound 1-(4-chlorophenyl)-3-(2,6-difluorobonzoyl)-urea (Diflubenzuron);
(6) the compound 1-(3,5-dichloro-4-[1,1,2,2-tetrafluoroethoxy]-phenyl)-3-(2,6-difluorobenzoyl)-urea (Hexaflumuron);
(7) the compound 1-(3,5-dichloro-2,4-dichloro-phenyl)-3-(2,6-difluorobenzoyl)-urea (Teflubenzuron);
(8) the compound 1-(3,5-dichloro-4-[3-chloro-5-trifluoromethyl-2-pyridyloxy]-phenyl)-3-(2,6-difluorobenzoyl)-urea (Chlorfluazuron);
(9) the compound 1-(2-chlorobenzoyl)-3-(4-trifluoromethoxyphenyl)-urea (Triflumuron);
(10) the compound 1-(4-[2-chloro-4-trifluoromethyl-phenoxy]-2-fluoro-phenyl)-3-(2,6-difluorobenzoyl)-urea (Flufenoxuron);
(11) the compound 1-[α-(4-chloro-α-cyclopropyl-benzylideneamino-oxy)-p-tolyl]-3-(2,6-difluorobenzoyl)-urea (Flucycloxuron);

and on the other hand at least one compound selected from any one of the following groups (12) to (21):
(12) a compound of formula II, wherein $R_5$ is methyl, ethyl, isopropyl or sec-butyl, especially methyl or ethyl;
(13) a compound of formula II, wherein X is

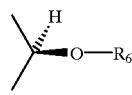

and $R_6$ is hydrogen or methyl, especially hydrogen;
(14) a compound of formula II, wherein X is

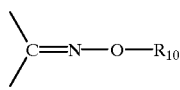

and $R_{10}$ is hydrogen or a methyl group, especially hydrogen;
(15) a compound of formula II, wherein $R_8$ is hydrogen or the group

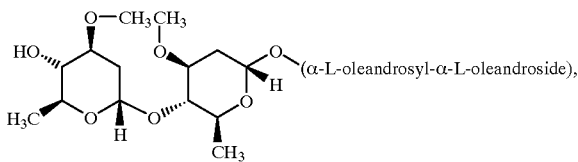

especially hydrogen;
(16) a compound of formula II, wherein the bond between the atoms 22 and 23 is a single bond and $R_7$ is hydrogen
(17) a compound of formula II, wherein $R_5$ is methyl, ethyl or isopropyl, especially methyl or ethyl, X is

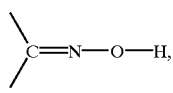

$R_7$ and $R_8$ arm hydrogen and the bond between the atoms 22 and 23 is a single bond;
(18) a mixture of two compounds of formula II, wherein X is

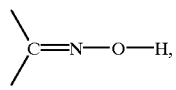

$R_7$ and $R_8$ are hydrogen, the bond between the atoms 22 and 23 is a single bond and, in approximately 20% by weight of the mixture, $R_5$ is methyl and, in approximately 80% by weight of the mixture, $R_5$ is ethyl;
(19) a compound of formula II, wherein X is

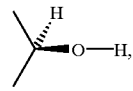

$R_7$ and $R_8$ are hydrogen, the bond between the atoms 22 and 23 is a single bond and
$R_5$ is methyl (milbemycin $A_3$), or
$R_5$ is ethyl (milbemycin $A_4$), or
$R_5$ is isopropyl (milbemycin D);
(20) a compound of formula II, wherein X is

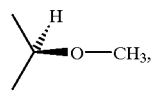

$R_8$ is α-L-oleandrosyl-α-L-oleandroside, and
a) the bond between the atoms 22 and 23 is a single bond, $R_7$ is OH and
$R_5$ is isopropyl (avermectin $A_{2b}$), or
$R_5$ is sec-butyl (avermectin $A_{2a}$); or
b) the bond between the atoms 22 and 23 is a double bond, $R_7$ is H and
$R_5$ is isopropyl (avermectin $A_{1b}$), or
$R_5$ is sec-butyl (avermectin $A_{1a}$);
(21) a compound of formula II, wherein X is

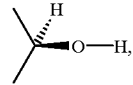

$R_8$ is α-L-oleandrosyl-α-L-oleandroside, and
a) the bond between the atoms 22 and 23 is a single bond, $R_7$ is OH and
$R_5$ is isopropyl (avermectin $B_{2b}$), or
$R_5$ is sec-butyl (avermectin $B_{2a}$); or
b) the bond between the atoms 22 and 23 is a double bond, $R_7$ is H and
$R_5$ is isopropyl (avermectin $B_{1b}$), or
$R_5$ is sec-butyl (avermectin $B_{1a}$).

Very especially preferred within the scope of the present invention is a composition, that comprises, as active ingredient, either
(22) Lufenuron and a mixture of two compounds of formula II, wherein X is

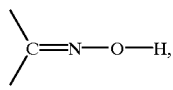

R₇ and R₈ are hydrogen. the bond between the atoms 22 and 23 is a single bond and R₅ is on the one hand methyl and on the other hand ethyl; or

(23) Fluazuron and a mixture of two compounds of formula II, wherein X is

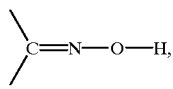

R₇ and R₈ are hydrogen, the bond between the atoms 22 and 23 is a single bond and R₅ is on the one hand methyl and on the other hand ethyl; or

(24) Lufenuron and milbomycin oxime.

The compounds of formulae I and II are known or can be prepared in accordance with methods that are known per se. Specifically:

Lufenuron is known from EP-B1-0 179 022;
Fluazuron from EP-A-0 079 311;
Diflubenzuron is known from The Pesticide Manual, 9$^{th}$ Ed. (1991), The British Crop Protection Council, London, page 281;
Teflubenzuron is known from The Pesticide Manual, 9$^{th}$ Ed. (1991), The British Crop Protection Council, London, page 790;
Chlorfluazuron is known from The Pesticide Manual, 9$^{th}$ Ed. (1991), The British Crop Protection Council, London, page 143;
Hexaflumuron is known from The Pesticide Manual, 9$^{th}$ Ed. (1991), The British Crop Protection Council, London, page 471;
Triflumuron is known from The Pesticide Manual, 10$^{th}$ Ed. (1994), The British Crop Protection Council, London, page 1023;
Flufenoxuron is known from The Pesticide Manual, 10$^{th}$ Ed. (1994), The British Crop Protection Council, London, page 483;
Flucycloxuron is known from The Pesticide Manual, 10$^{th}$ Ed. (1994), The British Crop Protection Council, London, page 478;
the compounds of formula II, wherein X is

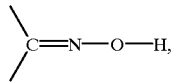

R₇ and R₈ are hydrogen, the bond between the atoms 22 and 23 is a single bond and R₅ is methyl or ethyl, are known under the terms milbemycin oxime A₃ (methyl derivative) and milbemycin oxime A₄ (ethyl derivative), respectively, and are described in EP-B 1-0 110 667;
milbemycin A₃ and milbemycin A₄ are known from U.S. Pat. No. 3,950,360;
milbemycin D is known from U.S. Pat. No. 4,346,171;
avermectin A$_{1a}$, avermectin A$_{1b}$, avermectin A$_{2a}$, avermectin A$_{2b}$, avermectin B$_{1a}$, avermectin B$_{1b}$, avermectin B$_{2a}$ and avermectin B$_{2b}$ are described in DE-OS 27 17 040.

It has now been found that the compositions according to the invention are outstandingly suitable for controlling pests in and on animals. In particular, it has surprisingly been found that the combination of one or more compounds of formula I with one or more compounds of formula II not only brings about an additive extension of the spectrum of activity towards the pests to be controlled, as was to be expected in principle, but also achieves a synergistic effect, which inter alla broadens the range of activity of the parasiticidal substances:

Firstly, the rates of application of the compounds of formula I and the compounds of formula II are reduced while the good activity remains unchanged. Secondly, the combined mixture achieves a high degree of pest control even where the two individual substances have become totally ineffective in the range of excessively low rates of application. This makes possible, on the one hand, a considerable broadening of the spectrum of pests that can be controlled and, on the other hand, increased safety in use. The term "synergy" may, however, be understood even more broadly: it is found that compositions that comprise an active ingredient mixture according to the invention can often be formulated better, for example can be ground, sieved and compressed better, than a single component, that the mixtures can often be emulsified or dispersed better, and that fewer problems arise in use, for example when spraying the mixtures, fewer problems arise with regard to blocking of the spray apparatus. In addition to having other advantages familiar to one skilled in the art, the mixtures often also have a distinctly better storage ability, for example are more stable to light and heat, than a single component, and the break-down behaviour in the soil can also have advantages over a single component.

The compositions according to the invention are valuable preventively and/or curatively in the field of controlling animal parasites, even at low rates of application, while being well tolerated by, for example, warm-blooded animals, fish and plants, and exhibit a very advantageous biocidal spectrum. The compositions according to the invention are effective against all or individual development stages of normally sensitive and also resistant animal pests, such as insects, representatives of the order Acarina or helminths. The good pesticidal activity of the compositions according to the invention may manifest itself directly, that is to say in the death of the pests, which occurs immediately or only at a later date, or indirectly, for example in a reduced oviposition and/or a reduced hatching rate of corresponding pests, the good activity corresponding to a mortality of at least 50 to 60%.

The pests which can be controlled with the compositions according to the invention include, for example:

of the order Acarina e.g. representatives of the families Argasidac, Ixodidae, Dermanyssidae, Sarcoptidae, Psoroptidae, Anocentor spp., Argas spp., Boophilus spp., Cheyletiella spp., Chorioptes spp., Demodex spp., Dermacentor spp., *Dermanyssus gallinae,* Haemophysalis spp., Hyalomma spp., Ixodes spp., Lynxacarus spp., Notoedres spp., Otodectes spp., Ornithodoros spp., Ornithonyssus spp., Otobius spp., Pneumonyssus spp., Psoroptes spp., Rhipicephalus spp., Sarcoptes spp.;

of the order Siphonaptera e.g. Ceratophyllus spp., *Xenopsylla cheopis* and Ctenocephalides spp., especially the species *C. felis* and *C. canis;* more especially *C. felis;* of the order Anoplura e.g. Haematopinus spp., Linognathus spp., Pediculus spp., Pemphigus spp., Phylloxera spp.;

of the order Mallophage e.g. Damalina spp., Felicola spp., Heterodoxus spp., Trichodectes spp.;

of the order Diptera for example Aedes spp., Anopheles spp., Calliphora spp., Chrysomyla spp., Chrysops spp., Cochliomyia spp., Culex spp., Culicoides spp., Cuterebra spp., Dermatobia spp., Gastrophilus spp., Glossina spp., Haematobia spp., Haematopota spp., Hypoderma spp., Hippobosca spp., Melophagus spp., Lucilia spp., Lyperosia spp., Oestrus spp., Phlebotomus spp., Phormia spp., Sarcophaga spp., Simulium spp., Stomoxys spp., Tabanus spp., Tannia spp., Tipula spp.;

of the class Trematoda especially representatives of the family Fasciolidae, especially *Fasciola hepatica;* of the class Nematoda for example the families Filariidae and Setariidac, especially the genera Haemonchus, Trichostrongylus, Ostertagia, Nematodirus, Cooperia, Ascaris, Bunostomum, Oesophagostomum, Chabertia, Trichuris, especially *Trichuris vulpis*, Strongylus, Trichonema, Dictyocaulus, Capillaria, Strongyloides, Heterakis, Toxocara, especially *Toxocara canis*, Ascaridia, Oxyuris, Ancylostoma, especially *Ancylostoma caninum*, Uncinaria, Toxascaris and Parascaris; Dirofilaria, especially *Dirofilaria immitis* (heart worm).

Most preferably, *Ctenocephalides felis* and/or *C. canis* are controlled simultaneously with *Dirofilaria immitis, Ancylostoma caninum, Toxocara canis* and/or *Trichuris vulpis*, and especially *C. felis* and *D. immitis* are controlled simultaneously on and in dogs.

These parasites infest numerous warm-blooded animals, for example cattle, horses, pigs, sheep, goats and poultry, and also fur-bearing animals, especially domestic animals, such as dogs and cats.

As is known, the life cycles of the various parasites are very complicated, which makes their control extraordinarily difficult. Ticks, for example, may feed exclusively on one host or also on several hosts. They settle on the host animal and feed on its blood. The females, fully replete with blood, drop off the host animal and then lay a large number of eggs in a suitable niche in the vicinity. The developing larvae then seek a new host animal in order to develop via the nymph stage into adults and once again become fully replete with blood. Certain species may migrate from one host animal to a second and even a third host animal.

Ticks that are of economic significance from the aetiological standpoint belong mainly to the genera Amblyomma, Boophilus, Hyalomma, Ixodes, Rhipicephalus and Dermacentor, but especially involved are the species *Boophilus microplus* and *B. annulatus*, most especially *B. microplus*. They arm responsible for the transmission of numerous diseases that may affect humans and animals. Bacterial, protozoan, rickettsial and viral diseases, in particular, arm transmitted. The causative organisms of such diseases are transmitted especially by ticks that feed on more than one host. These diseases may lead to weakening or even death of the host animals. They usually cause high economic losses, for example as a result of the meat of productive livestock losing value, the usable skin being damaged or milk production being reduced.

Ticks of the species listed above are normally controlled by treating the affected animals with an acaricidally active composition in response to an actual infestation, that is to say curatively. The occurrence of ticks, for example on pasture, is greatly dependent, however, upon seasonal weather conditions, and the ultimate infestation of the host animals depends, in addition, upon their resistance to the ticks. This means that a preventive control of the ticks is difficult and time-consuming since inter alia the risk of infestation by the pests and the animals' power of resistance to them can be estimated only with difficulty. In addition, when attempting a preventive control of the parasites, the potential infestation has to be monitored over a relatively long period, which causes additional problems. The reason why a curative control of the pests is normally aimed at is not primarily, therefore, because relatively great damage has often already occurred by the time the control begins to act.

Owing to the complicated life cycle of fleas, none of the known methods for their control gives all round satisfaction, especially since most of the known control methods rely upon the active substance or active substances being applied to the habitat of the various flea stages. In view of the complex life cycle of fleas, however, this method is very laborious and unreliable.

If the control is targeted, for example, at treatment of the fully grown fleas in the coat, which is usually accomplished by applying an anti-flea composition to the coat of the host animal, the different, juvenile stages of the fleas, which live not only in the coat of the animal but also mainly on the floor, on carpets, where the animal sleeps, on chairs, in the garden and all the other places with which the infested animal comes in contact, are totally disregarded.

For example, adult cat and dog fleas (*Ctenocephalides felis* and *C. canis*) normally live in the coat of the host cat and host dog. They feed on the blood of the host animal and lay their eggs in its coat. Since those eggs are not self-clinging, however, they generally soon fall off and can be found on the floor, on carpets, in the dog basket or cat basket, on chairs used by the animal, in the garden and so on.

This means that the entire area where the animals live is contaminated with flea eggs from which, within two days, the larvae develop. In the case of the larvae, a distinction is made between three stages of development, each of which lasts three days. In the last stage, the larvae spin their cocoons and change into pupae from which the young, mature fleas develop. The young adult fleas remain there until they sense the presence of an acceptable host animal, then they emerge from their cocoons and attempt to jump onto the host animal. It takes about three weeks, therefore, before an adult young flea capable of re-infesting the host animal develops from an egg.

The young flea may, however, remain in its cocoon for months, possibly up to a year. On the other hand, under less than optimum conditions, development from egg to adult young flea may take 4 to 5 months. Fleas require blood as food to reach their sexual maturity in order to reproduce. Flea larvae feed mainly on the excreta of the adult fleas that live on the host animal. Those excreta contain high proportions of undigested blood.

This long life cycle, which takes place away from the host animal, has a significant effect on the successful control of fleas on the host animal.

Only when the described cycle can be broken, that is to say when the numerous flea eggs and flea larvae present in the environment of the host animal can be destroyed, is the animal protected from continual re-infestation by adult parasites.

Flea infestation of animals, especially dogs and cats, has unpleasant accompaniments not only for the animal to be treated but also for the keeper of the animal. Such unpleasant effects lead, for example, to local irritation, annoying itchiness or even to allergies and often cause intense scratching. Furthermore, animals infested with fleas are constantly exposed to the risk of being infected with representatives of Dipylidium spp., that is to say tape worms, which are transmitted by fleas.

In addition, fleas and their excreta may also lead to allergy-like skin disorders in some people, which in many cases forces them to give up keeping the animal. An effective control of fleas in productive livestock and pets, especially dogs and cats, has therefore been desirable since time immemorial.

A number of conventional methods of control are known which, however, have various disadvantages. If, for example, flea combs which arm surface-coded with an insecticide are used, the keeper of the animal has to comb the animal intensively and frequently. The use of corresponding anti-flea shampoos is not possible in many cases since most of the animals infested can be bathed only with difficulty, if at all. Moreover, the effect of such a bath treatment lasts for about a week at most. The same problems are to be reckoned with when using oil rubs or rinses. The animal also does not generally submit, without some resistance, to the use of powders. It is virtually unavoidable that the human also will come into contact with the composition to a greater or lesser extent.

When sprays are used, most animals, especially cats, take to flight or react aggressively at the mere noise of the spray. Furthermore, sprays also have all the disadvantages mentioned in connection with powders, added to which they are even more finely dispersed in the atmosphere and therefore can be inhaled by man and animal. Frequently, fleas are also controlled with so-called flea collars, which show a good effect temporarily. One weakness found with this treatment, however, is the locally very limited application.

Previous methods, which aimed at killing the adult flea, provide such unsatisfactory results mainly because they depend upon the patience and skill of the user in dealing with the infested host animal. The previous methods are relatively laborious, time-consuming and not particularly promising in the long term. In the short term, however, it is perfectly possible to achieve alleviation with the conventional compositions.

Something that has previously not been given sufficient attention in the case of the conventional methods and compositions is the fact that, because of the particular life cycle of the flea, the host animals are re-infested over and over again, on the one hand because contact with the flea eggs, flea larvae and young adult fleas on the floor and in the immediate environment of the animal is unavoidable and, on the other hand, because many animals come into contact again and again with infested members of their own species.

With conventional compositions, continual re-infestation is not adequately prevented or prevention is achievable only with high application rates of parasiticides.

In numerous regions of the world, the conditions under which domestic animals and pets are kept greatly encourage the spread of not only ectoparasites but also, in particular, endoparasites. These parasites include especially the pests generally referred to as helminths, which may infest pigs, sheep, cows, calves, goats, horses, dogs, cats and poultry. Helminthiases are a serious economic and hygiene problem in these domesticated animals. They lead to anaemia, malnutrition, infirmity, weight loss, damage to the walls of the intestinal tract and to other organs and may, if not treated, result in the death of the animal affected. Among the helminths, especially the group of the roundworms or nematodes causes an often serious infection of the animals. Representatives of the genera Nematodirus, Cooperia and Oesophagostomum live in the intestines, while parasites of the genera Haemonchus and Ostertagia live in the stomach, and those of the genus Dictyocaulus are to be found in the lungs. Parasites of the families Filariidac and Setariidae affect mainly the heart, the blood vessels and the lymph vessels.

Other examples of endoparasites that are capable of causing great damage are representatives of the genus Dirofilaria, especially *Dirofilaria immitis* (heart worm), especially in dogs.

Surprisingly, it has now been found that, with the aid of specific methods of administration, for example by external treatment but especially by systemic administration, and using a composition that comprises as active ingredients one or more compounds of formula I and one or more compounds of formula II or the salts thereof, it is possible to eliminate the mentioned ectoparasites very quickly and completely and thereby intervene obstructively in the complex development cycle of the parasites, and at the same time achieve effective control of the endoparasites. Since these compositions still display their excellent parasidcidal effect fully when administered to the host animal systemically, i.e. orally, parenterally, subcutaneously, intramuscularly or intravenously, it is possible by controlled periodic administration of them to interrupt the described continually recurring re-infestation of the host animals by the various parasites in a simple manner, until all the young stages in the area where the host animal lives have been controlled. The parasites are killed and prevented from reproducing, and the juvenile stages are prevented from reaching adulthood and can no longer infest the host animal, as a result of which the area where the host animals live can be kept free of parasites permanently.

The present invention further relates therefore, to a method of controlling parasites in and on domestic animals and productive livestock, which comprises administering to the host animal a composition comprising at least one compound of formula I and at least one compound of formula II or a salt thereof, in a parasidcidally effective amount, orally, parenterally or by implant. A special form of this method comprises administering the different active ingredients that are to be used to the host animal, in a parasiticidally effective amount, not simultaneously but within a short interval, that is to say within one week at most, especially on the same day. In that method, it makes no difference whether the modes of administration are identical, that is to say whether the active ingredients are all administered for example orally, or are different, that is to say whether one or more of the active ingredients is/are administered for example orally and others are administered, after a short interval, for example subcutaneously.

What is very remarkable with regard to the present invention is that the full effect is still achieved even when the active ingredient mixture is administered to the host animal in relatively low concentrations. With the endo- and ectoparasites being killed completely and simultaneously after systemic administration of the active substances, it is now possible to achieve simultaneous elimination of the parasites. By combining this systemic use of the active substances with secondary measures, such as disinfection of the abode of the host animal, it is possible to dispose of the parasite problem even more quickly; even without those secondary measures, however, the parasite population will be reduced completely or at least to an acceptable minimum within a few weeks or, at most, months.

The complex life cycles of, for example, fleas and ticks are interrupted, therefore, and continual re-infestation of the host animals in their preferred living area by the eggs that are scattered everywhere and by the larvae that emerge therefrom is prevented. The way in which the parasites are controlled is that, although eggs are laid by the adults that are fully replete with blood, which, in the case of ticks, drop off the host animal but, in the case of fleas, remain on the host animal, no larvae or only few larvae are able to develop from those eggs. While those few larvae can in turn infest the host animal, they are unable to develop further, whereby the cycle is broken. The compositions according to the invention therefore have especially a preventive effect against the various types of parasite, but also have a curative effect inasmuch as, for example, tick larvae that are on the host animal but have not yet ingested any active substance via the described cycle are also prevented from developing further into adults upon treatment of the host with a topical pour-on or spot-on formulation.

An important advantage of the method according to the invention resides in the fact that the life cycle of carriers also is interrupted. These are, for example, various species of mosquito that are responsible for transmitting endoparasites, such as Filariae.

The present invention accordingly encompasses two aspects, on the one hand the method of preventing re-infestation of pets and productive livestock by parasites which has already been described and, at the same time, the suppression of reproduction of the said parasites.

It is essential to the invention that the composition according to the invention is so administered that the active substances which the composition comprises can be ingested by endoparasites, ectoparasites, and also by other pests that come into consideration as vectors for the transmission of endoparasites, with the blood of the host animal in an amount sufficient that the eggs laid by the adults and also the larvae no longer develop.

This is achieved with the composition according to the invention using various forms of administration, for example by administering the composition comprising the active ingredients orally. "Formulated" means in this case, for example, in the form of a powder, a tablet, granules, a capsule, an emulsion, a foam, in microencapsulatod form etc., the formulation not necessarily having to be given to the animal directly but advantageously being mixed with its food. All compositions that are to be administered orally may, of course, contain, in addition to customary formulation adjuvants, also other additives that encourage voluntary intake by the host animal, for example suitable flavourings. Owing to its easy practicability, oral administration is one of the preferred objects of this invention. Another mode of administration is parenteral administration, for example subcutaneous or intravenous injection, topical application or, as a long-term formulation (depot form), in the form of an implant or injection of microcapsules (so-called "microspheres").

Oral administration includes, for example, the serving of animal food, for example of dog and cat food, that already contains the active substances mixed with it, for example in the form of biscuits, in the form of lozenges, water-soluble capsules or tablets, in water-soluble form which can be added in drops to the food, or in other formns that can be admixed with the animal food. Implants also include all devices that can be inserted into the body of the animal to release the substances.

Percutaneous forms of administration include, for example, subcutaneous, dermal, intramuscular and even intravenous administration of injectable forms. Apart from conventional syringes with needles, needleless pressure gun devices and also pour-on and spot-on formulations may be useful for this purpose.

By choosing a suitable formulation it is possible to enhance the penetration capacity of the active ingredients through the living tissue of the animal and maintain its availability. This is important when, for example, one or more sparingly soluble active ingredients are used, the low solubility of which necessitates a measure that promotes solubility since the body fluid of the animal is capable of dissolving only small amounts of the active ingredients all at once.

The active ingredients may also be present in a matrix formulation which, by physical means, prevents their decomposition and maintains the constant availability of the active ingredients. This matrix formulation is injected into the body and remains there as a kind of depot from which the active ingredients are continuously released. Such matrix formulations are known to one skilled in the art. They are generally wax-like, semi-solid excipients, for example vegetable waxes and polyethylene glycols having a high molecular weight, or copolymers of degradable polyesters.

High availability of the active ingredients is also obtained by inserting an implant of the active substances into the animal. Such implants are widely used in veterinary medicine and often consist of silicone-containing rubber. The active substances are dispersed in the solid rubber or located inside a hollow rubber body. Care should be taken to select active substances that are soluble in the rubber implant since they are first dissolved in the rubber and then seep continuously from the rubber material into the body fluid of the animal to be treated.

The release rate of the active substances from the implant, and hence the period for which the implant is effective, is generally determined by the accuracy of calibration (amount of active ingredient in the implant) of the implant, the environment of the implant and the polymer formulation from which the implant is made.

The administration of the active ingredients by means of implant is another preferred component of the present invention. Administration in that manner is extremely economical and effective, since a correctly dimensioned implant ensures a constant concentration of the active substances in the tissue of the host animal. Implants can nowadays be fashioned and easily implanted in such a manner that they are capable of delivering the active ingredients over a number of months.

The administration of veterinary medicine additives to animal food is best known in the animal health sector. Usually, a so-called premix is prepared first, in which the active substances are dispersed in a liquid or finely distributed in solid carriers. That premix may normally comprise, depending upon the desired final concentration in the food, approximately from 1 to 800 g of the substances per kg of premix.

In addition, it is known that active ingredients may be hydrolysed or made weaker by the ingredients of the food. Such active substances are routinely formulated in a protective matrix, e.g. in gelatin, before being added to the premix.

The compounds of formulae I and II are advantageously administered in a dose of from 0.01 to 800, preferably from 0.1 to 200, especially from 0.5 to 30, mg/kg of body weight based on the host animal, oral administration being preferred.

A good dose to be administered regularly to the host animal is especially, in the case of cats, 30 mg/kg body weight of a compound of formula I and 2 mg of a compound of formula II and, in the case of dogs, 10 mg/kg body weight of a compound of formula I and 0.5 mg/kg body weight of a compound of formula II. Administration is advantageously carried out weekly or monthly, especially monthly.

The total dose may vary for the same active ingredient from one genus of animal to another and also within one animal genus since it depends inter alia upon the weight and constitution of the animal.

The good pesticidal action of the compositions according to the invention corresponds to a mortality of at least 50–60% of the mentioned pests.

The composition according to the invention normally comprises from 0.1 to 99% by weight, preferably 0.1 to 95% by weight, of a compound of formula I and from 99.9 to 1% by weight, preferably from 99.9 to 5% by weight, of a solid or liquid adjuvant, including from 0 to 25% by weight, preferably from 0.1 to 25% by weight, of a surfactant.

The active ingredient combination according to the invention comprises one or more active ingredients of formula I and one or more active ingredients of formula II preferably in a mixing ratio of from 1:50 to 50:1, especially in a ratio of from 1:20 to 20:1, more especially from 10:1 to 1:10, most especially from 5:1 to 1:5, and most preferably from 2:1 to 1:2. Especially preferred mixing ratios of an active ingredient of formula I with an active ingredient of formula II are also 20:1, 15:1, 5:1, or 4:1, or 3:1, or 2:1, or 1:1, or 1:2, or 1:3, or 1:4, or 1:5, or 5:2, or 3:2, or 4:3, or 3:4, or 2:3, or 5:3, or 3:5, or 5:4, or 4:5.

Whereas commercial products will preferably be formulated as concentrates, in cases where the active ingredient mixture still needs to be dissolved at all or needs to be emulsified or dispersed, the end user will normally employ dilute formulations.

Such formulations may also comprise further auxiliaries, such as stabilisers, antifoams, viscosity regulators, binders and also tackifiers.

As formulation adjuvants there may be used the materials known from veterinary medicine for oral and parenteral administration and implants. A number of examples are mentioned below.

Suitable carriers are especially fillers, such as sugars, for example lactose, saccharose, mannitol or sorbitol, cellulose preparations and/or calcium phosphates, for example tricalcium phosphate or calcium hydrogen phosphate, and also binders, such as starch pastes using, for example, corn, wheat, rice or potato starch, gelatin, tragacanth, methylcellulose, and/or, if desired, disintegrators, such as the above-mentioned starches, also carboxymethyl starch, crosslinked polyvinylpyrrolidone, agar, alginic acid or a salt thereof, such as sodium alginate. Excipients are especially flow conditioners and lubricants, for example silicic acid, talc, stearic acid or salts thereof, such as magnesium or calcium stearate, and/or polyethylene glycol. Dragée cores may be provided with suitable, optionally enteric, coatings, there being used, inter alia, concentrated sugar solutions which may comprise gum arabic, talc, polyvinylpyrrolidone, polyethylene glycol and/or titanium dioxide, or coating solutions in suitable organic solvents or solvent mixtures, or, for the preparation of enteric coatings, solutions of suitable cellulose preparations, such as acetylcellulose phthalate or hydroxypropylmethylcellulose phthalate. Dyes, flavourings or pigments may be added to the tablets or dragée coatings, for example for identification purposes or to indicate different doses of active ingredient.

Other orally administrable compositions are dry-filled capsules made of gelatin and also soft, sealed capsules made of gelatin and a plasticiser, such as glycerol or sorbitol. The dry-filled capsules may comprise the active ingredients in the form of granules, for example in admixture with fillers, such as lactose, binders, such as starches, and/or glidants, such as talc or magnesium stearate, and, if desired, stabilisers. In soft capsules, the active ingredients are preferably dissolved or suspended in suitable liquids, such as fatty oils, paraffin oil or liquid polyethylene glycols, to which stabilisers may also be added. Preferred inter alia are capsules that can be both easily bitten and swallowed unchewed.

Suitable for parenteral administration are especially aqueous solutions of the active ingredients in water-soluble form, e.g. in the form of water-soluble salts, or also suspensions of the active ingredients, such as corresponding oily injection suspensions, there being used suitable lipophilic solvents or vehicles, such as fatty oils, e.g. sesame oil, or synthetic fatty acid esters, e.g. ethyl oleate, or triglycerides, or aqueous injection suspensions that comprise viscosity-increasing substances, e.g. sodium carboxymethylcellulose, sorbitol and/or dextran, and, if desired, also stabilisers.

The compositions according to the invention may be prepared in a manner known per se, for example by means of conventional mixing, granulating, confectoning, dissolving or lyophilising processes. For example, pharmaceutical comprisidons for oral administration can be obtained by combining the active ingredients with solid carriers, if desired granulating a resulting mixture, and processing the mixture or granules, if desired or necessary after the addition of appropriate excipients, to form tablets or dragée cores.

The following Examples illustrate the invention described above but do not limit the scope thereof in any way. Temperatures are given in degrees Celsius.

FORMULATION EXAMPLES

In the following Formulation Examples, the expression "active ingredient I" denotes one or more compounds of formula I and "active ingredient II" denotes one or more compounds of formula II or a salt thereof.

Example 1

Tablets Comprising Active Ingredients I and II Can be Prepared in the Following Manner:

| Constituents (for 1000 tablets) | |
| --- | --- |
| active ingredient I | 25 g |
| active ingredient II | 1.25 g |
| lactose | 100.7 g |
| wheat starch | 6.25 g |
| polyethylene glycol 6000 | 5.0 g |
| talc | 5.0 g |
| magnesium stearate | 1.8 g |
| demineralised water | q.s. |

Preparation: All the solid ingredients are first forced through a sieve of 0.6 mm mesh size. Then the active ingredient, the lactose, the talc and half of the starch are mixed. The other half of the starch is suspended in 40 ml of water and the suspension is added to a boiling solution of the polyethylene glycol in 100 ml of water. The resulting starch paste is added to the main ingredients and the mixture is granulated, if necessary with the addition of water. The granules are dried overnight at 35°, forced through a sieve of 1.2 mm mesh size, mixed with the magnesium stearate and compressed to form biconcave tablets of approximately 6 mm mesh size.

Example 2

Tablets Comprising a Total of 0.0183 g of Active Ingredient are Prepared as Follows:

| Composition (for 10000 tablets) | |
|---|---|
| active ingredient I | 180.00 g |
| active ingredient II | 3.0 g |
| lactose | 290.80 g |
| potato starch | 274.70 g |
| stearic acid | 10.00 g |
| talc | 217.00 g |
| magnesium stearate | 2.50 g |
| colloidal silica | 32.00 g |
| ethanol | q.s. |

A mixture of the active ingredients, the lactose and 200 g of potato starch is moistened with an ethanolic solution of the stearic acid and granulated through a sieve. After drying the granules, the remainder of the potato starch, the talc, the magnesium stearate and the colloidal silica are added thereto and the mixture is compressed to form tablets each weighing 0.1 g which may, if desired, be provided with breaking notches for finer adjustment of the dose.

Example 3

Capsules Comprising a Total of 0.022 g of the Active Ingredients can be Prepared as Follows:

| Composition (for 1000 capsules) | |
|---|---|
| active ingredient I | 20.00 g |
| active ingredient II | 2.00 g |
| lactose | 249.80 g |
| gelatin | 2.00 g |
| corn starch | 10.00 g |
| talc | 15.00 g |
| water | q.s. |

The active ingredient is mixed with the lactose and the mixture is uniformly moistened with an aqueous solution of the gelatin and granulated through a sieve having a mesh size of 1.2–1.5 mm. The granules are mixed with the dried corn starch and the talc, and portions of 300 mg are introduced into hard gelatin capsules (size 1).

Example 4

Premix (food additive)

| | |
|---|---|
| 0.15 | part by weight of active ingredient I |
| 0.01 | part by weight of active ingredient II and |
| 4.84 | parts by weight of secondary calcium phosphate, argillaceous earth, Aerosil, carbonate or chalk are mixed with |
| 95 | parts by weight of an animal food until homogeneous. |

Example 5

Premix (food additive)

| | |
|---|---|
| 0.40 | part by weight of active ingredient I |
| 0.01 | part by weight of active ingredient II and |
| 5.00 | parts by weight of Aerosil/chalk (1:1) are mixed with |
| 94.59 | parts by weight of a commercial dry food until homogeneous. |

Example 6

Emulsifiable Concentrate

| | |
|---|---|
| 20 | parts by weight of active ingredient I and |
| 1 | part by weight of active ingredient II are mixed with |
| 20 | parts by weight of the emulsifier, e.g. a mixture of alkylaryl polyglycol ether with alkylaryl polysulfonates, and with |
| 59 | parts by weight of a solvent until the solution has been completely homogenised. Emulsions of the desired concentration are obtained by dilution with water. |

Example 7

Soluble Powder

| | |
|---|---|
| 25 | parts by weight of active ingredient I |
| 0.5 | part by weight of active ingredient II |
| 2.5 | parts by weight of sodium lauryl sulfate |
| 3 | parts by weight of colloidal silica gel, and |
| 69 | parts by weight of urea. |

The constituents are mixed and ground together until homogeneous.

Other biologically active substances or additives that have a neutral behaviour towards the active ingredients and do not have any harmful effect on the host animal to be treated, and also mineral salts or vitamins may be added to the described compositions.

BIOLOGICAL EXAMPLES (unless defined otherwise, %=percent by weight)

Example 8

Simultaneous Action Against *Ancylostoma caninum* and *Ctenocephalides felis*

As test animals, 3 dogs (1 female, 2 male) of from 7 to 10.5 kg body weight and from 2 to 3 years of age are used. As comparison animals, 3 dogs (1 female, 2 male) of from 7.5 to 10 kg body weight and from 2 to 4 years of age are used. All the animals ame naturally infected with *Ancylostoma caninum*. Immediately after administration of a gelatin capsule comprising 10 mg/kg body weight of Lufenuron and 0.5 mg/kg body weight of a mixture of milbemycin oxime $A_3$ and milbemycin oxime $A_4$, the test animals are each infested in the neck region with 20 fleas of the species *Clenocephalides felis* (16 female and 4 male fleas). The comparison animals are not given any active substances but are infected in the same manner and at the same time with *Ctenocephalides felis*.

During the test period, the flea eggs are collected daily and incubated to determine their viability. A first evaluation of the endoparasites is carried out by comparing the number of worms excreted by the test animals and the control animals. Only a few days after the treatment, the hatching rate of the flea eggs and their development into adult fleas is completely suppressed. An autopsy reveals that the test animals are completely free of worms. In the untreated animals, neither a significant reduction in the ability of the flea eggs to develop nor a reduction in the number of worms in the gastrointestinal tract is found.

Example 9

Simultaneous Action Against *Ctenocephalides felis* and *Dirofilaria immitis*

As test animals, 3 dogs (1 female, 2 male) of from 7.5 to 10.2 kg body weight and from 2 to 4 years of age are used. As comparison animals, 3 dogs (1 female, 2 male) of from 7.0 to 10.1 kg body weight and from 2 to 4 years of age are used. The test animals are infected subcutaneously with 40 infectious larvae (3rd larval stage) of *Dirofilaria immitis* obtained from infected mosquitoes (*Aedes aegypti*). 30 days later, they are given a gelatin capsule comprising 10 mg/kg body weight of Lufenuron and 0.5 mg/kg body weight of a mixture of milbemycin oxime $A_3$ and milbemycin oxime $A_4$. Immediately after administration of the gelatin capsule comprising the active substances, the test animals are each infested in the neck region with 20 fleas of the species *Ctenocephalides felis* (16 female and 4 male fleas). The comparison animals arm not given any active substances but are infected in the same manner and at the same time with *Dirofilaria immitis* and *Ctenocephalides felis*. Only a few days after the treatment, the hatching rate of the flea eggs and their development into adult fleas is completely suppressed.

Upon autopsy 200 days after infection, adult heart worms are no longer found in the lungs and heart of the treated animals. In the untreated control group, on average 20 adult specimens of *Dirofilaria immitis* are found per test animal.

What is claimed is:

1. A composition for controlling parasites comprising an effective amount of at least one compound of the formula (I)

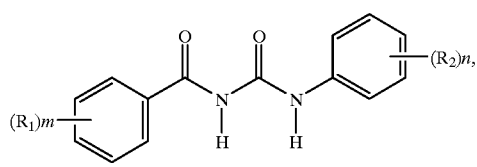

(I)

wherein $R_1$ is halogen, $C_1$–$C_8$alkyl, $C_3$–$C_8$cycloalkyl, halo-$C_3$–$C_8$cycloalkyl, halo-$C_1$–$C_8$alkyl, $C_1$–$C_8$alkoxy, $C_1$–$C_4$alkoxy-$C_1$–$C_4$alkyl or halo-$C_1$–$C_8$alkoxy, $R_2$ is halogen, $C_1$–$C_8$alkyl, $C_3$–$C_8$cycloalkyl, halo-$C_1$–$C_8$alkyl, halo-$C_3$–$C_8$cycloalkyl, $C_1$–$C_8$alkoxy, $C_3$–$C_8$cycloalkoxy, halo-$C_1$–$C_8$alkoxy, halo-$C_3$–$C_8$cycloalkoxy, aryloxy or heteroaryloxy, substituted aryloxy or heteroaryloxy or a group —$CH_2$—O—N=C($R_3$)$R_4$, wherein $R_3$ and $R_4$ are each, independently of the other, $C_1$–$C_4$alkyl, $C_3$–$C_8$cycloalkyl or aryl, each of which is unsubstituted or substituted;

m is 0 to 5, and, when m is greater than 1, the radicals $R_1$ are the same or different; and n is 0 to 5, where, when n is greater than 1, the radicals $R_2$ are the same or different;

in free form or in salt form, and at least one compound of the formula (II)

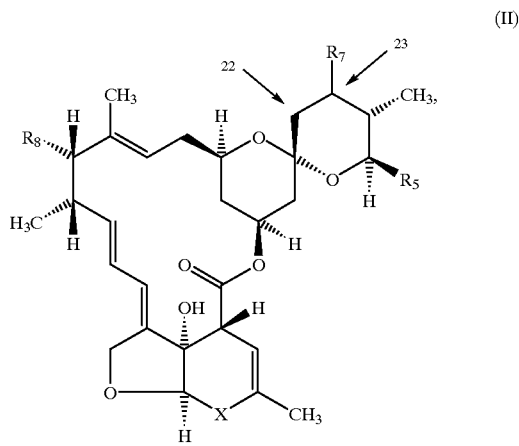

(II)

wherein $R_5$ is $C_1$–$C_4$alkyl or $C_2$–$C_4$alkenyl, the bond between atoms 22 and 23 is a single bond or a double bond X is a group

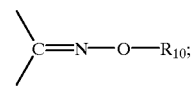

$R_7$ is hydrogen or hydroxy, $R_7$ being hydrogen when the bond between atoms 22 and 23 is a double bond;

$R_8$ is hydrogen, $C_1$–$C_8$alkyl, $C_2$–$C_8$alkenyl, aryl, substituted aryl or a group —$OR_9$ or —$SR_9$, $R_9$ is $C_1$–$C_8$alkyl, $C_2$–$C_8$alkenyl, $C_2$–$C_8$alkynyl, aryl, C(=O)$R_{16}$, substituted $C_1$–$C_8$alkyl, $C_2$–$C_8$alkenyl, $C_2$–$C_8$alkynyl, or aryl, or an unsubstituted or substituted heterocyclic radical;

$R_{10}$ is hydrogen, unsubstituted or substituted $C_1$–$C_8$alkyl, aryl-$C_1$–$C_4$alkyl, —$(CH_2)_o COR_{11}$ or —$SO_2$—$R_{15}$;

$R_{11}$ is hydrogen, $C_1$–$C_8$alkyl, aryl-$C_1$–$C_8$alkyl, $C_2$–$C_8$alkenyl, $C_2$–$C_8$alkynyl, $C_1$–$C_8$alkoxy, $C_2$–$C_8$alkenyloxy, $C_2$–$C_8$alkynyloxy, aryl, aryloxy, —$N(R_{12})R_{13}$, —$(CH_2)_p COOR_{14}$, or $C_1$–$C_8$alkyl or $C_1$–$C_8$alkoxy substituted by $C_1$–$C_4$alkoxy, halogen or by nitro, or aryl, aryloxy or aryl-$C_1$–$C_8$alkyl substituted by $C_1$–$C_4$alkyl, halo-$C_1$–$C_4$alkyl, $C_1$–$C_4$alkoxy, halo-$C_1$–$C_4$alkoxy, halogen or by nitro;

$R_{12}$ and $R_{13}$ are each, independently of the other, hydrogen, $C_1$–$C_8$alkyl, phenyl, or $C_1$–$C_8$alkyl or phenyl substituted by $C_1$–$C_4$akoxy, halogen or by nitro;

$R_{14}$ is hydrogen or unsubstituted or substituted $C_1$–$C_8$alkyl;

$R_{15}$ is $C_1$–$C_8$alkyl or aryl, each of which is unsubstituted or substituted;

$R_{16}$ is hydrogen, $C_1$–$C_8$alkyl, $C_1$–$C_8$alkoxy or aryl, each of which is unsubstituted or substituted;

o is 0, 1, 2, 3 or 4; and p is 0, 1, 2, 3 or 4;

in free form or in salt form;

and a suitable carrier.

2. The composition according to claim 1 which comprises the compounds in free form.

3. The composition according to claim 1 which comprises 1-[2,5-dichloro-4-(1,1,2,3,3,3-hexafluoroprop-1-oxy) phenyl-3-(2,6-difluorobenzoyl)urea.

4. The composition according to claim 1 which comprises 1-[3-(3-chloro-5-trifluoromethyl-pyrid-2-yloxy)-4-chlorophenyl]-3-(2,6-difluorobenzoyl)urea.

5. The composition according to claim 3 further comprising milbemycin oxime.

6. The composition according to claim 4 further comprising milbemycin oxime.

7. An animal feed comprising the composition according to claim 1.

8. The composition according to claim 1 in an amount effective to control parasites on a dog or cat.

9. The composition according to claim 1 wherein the parasites are selected from the group consisting of insects, acarina and worms.

10. The composition according to claim 1 wherein the parasites comprise ectoparasites of the species *Ctenocephalides felis* or *C. canis* or endoparasites of the species *Ancylostoma canium, Dirofilaria immitis, Toxocara canis* or *Trichuris vulpis*, or combinations thereof.

11. The composition according to claim 10 wherein the parasites comprise ectoparasites of the species *Ctenocephalides felis* or endoparasites of the species *Dirofilaria immitis*, or a combination thereof.

* * * * *

UNITED STATES PATENT AND TRADEMARK OFFICE
CERTIFICATE OF CORRECTION

PATENT NO.    : 6,201,012 B1                                  Page 1 of 1
DATED         : March 13, 2001
INVENTOR(S)   : Lowndes et al.

It is certified that error appears in the above-identified patent and that said Letters Patent is hereby corrected as shown below:

<u>Title page,</u>
Section titled "OTHER PUBLICATIONS" should read, Interceptor, Flavour Tabs, Aug. 1994.
Section *"Primary Examiner"* should read -- Primary Examiner-Jose' G. Dees <u>Column 20,</u>
Line 40 should read --$C_2$-$C_8$alkynyl or aryl, or an unsubstituted or substituted --
Line 54 should read -- nyl substituted by $C_1$-$C_4$alkoxy, halogen or by nitro; --

Signed and Sealed this

Eighteenth Day of December, 2001

Attest:

JAMES E. ROGAN
*Attesting Officer*      *Director of the United States Patent and Trademark Office*